United States Patent [19]

Wu

[11] Patent Number: 5,981,597
[45] Date of Patent: Nov. 9, 1999

[54] DIFFERENTIATING AGENTS FOR THE TREATMENT OF INFLAMMATORY INTESTINAL DISEASES

[75] Inventor: Gary Dean Wu, Ardmore, Pa.

[73] Assignee: Trustees of the University of Pennsylvania, Philadelphia, Pa.

[21] Appl. No.: 08/413,806

[22] Filed: Mar. 30, 1995

Related U.S. Application Data

[63] Continuation-in-part of application No. 08/387,116, Feb. 13, 1995, Pat. No. 5,569,680.

[51] Int. Cl.$^6$ .............................. A01N 37/18; A01N 37/02
[52] U.S. Cl. ............................................. 514/616; 514/557
[58] Field of Search .................................... 514/786, 557, 514/616; 536/4.1

[56] References Cited

U.S. PATENT DOCUMENTS

| | | | |
|---|---|---|---|
| 4,200,647 | 4/1980 | Bollag et al. | 424/305 |
| 5,369,108 | 11/1994 | Breslow et al. | 514/266 |
| 5,446,035 | 8/1995 | Neef et al. | 514/167 |
| 5,852,056 | 12/1998 | Samid | 514/510 |

OTHER PUBLICATIONS

Medline Abstract 89127883, Morassi et al. Minerva Medica 80(1):65–70, 1989.
Biosis Abstract No. 91:522751, Guillemot et al., Dis Colon Rectum 34(10):861–864, 1991.
Kelly et al. Am. J. Physiol. 267:pG991–7,1994.
Barnard et al., "Localization of Tranforming Growth Factor β Isoforms in the Normal Murine Small Intestine and Colon," *Gastroenterolgy* (1993), 105:67–73.
Biasco et al., "Proliferative and Antigenic Properties of Rectal Cells in Patients with Chronic Ulcerative Colitis," *Cancer Res.* (1984), 44:5450–5454.
Bikle et al., "Vitamin D, Caldium and Epidermal Differentiation," *Endocrin Reviews* (1993), 14(1):3–19.
Bland, P., "MHC Class Ii Expression by the Gut Epithelium," *Immuno. Today* (1988). 9:174–178.
Breuer et al., "Rectal Irrigation with Short–Chain Fatty Acids for Distal Ulcerative Colitis", *Dig. Dis. Sci.* (1991), 36:185–187.
Cao et al., "Regulated Expression of Three C/EBP Isoforms during Adipose Conversion of 3T3–L1 Cells," *Genes and Develop.* (1991), 5:1538–1552.
Chen, Z. and Breitman, T.R., "Tributyrin: A Prodrug of Butyric Acid for Potential Clinical Application in Differentiation Therapy", *Cancer Research* (1994) 54:3494–3499.
Chomczynski, P. and Sacchi, N., "Single–Step Method of RNA Isolation by Acid Guanidinium Thiocyanate–Phenol–Chloroform Extraction", *Anal. Biochem.* (1987) 162:156–159.
Gordon, J.I, "Intestinal Epithelial Differentiation: New Insights form Chimeric and Transgenic Mice," *J. Cell. Biol.* (1989), 108:1187–1194.
Halline et al., "Effects of 1,25–Dihydroxyvitamin $D_3$ on Proliferation and Differentiation of Caco–2 Cells," *Endocrinology* (1994), 134(4):1710–1717.

Hawkey et al.,"Therapeutic Interventions in Gastrointestinal Disease based on an Understanding of Inflammatory Mediators," *Agents Actions* (1992), 92:c22–26.
Huang et al. "Overexpression of a Trucated Growth Hormone Receptor in the Sex–Linked Dwarf Chicken: Evidence for a Splice Mutation", *Mol. Endo.* (1993), 7:1391–1398.
Izzo et al., In Situ Reverse Transcription PCR of Interleukin–8 mRNA Colonic Mucosa from Patients with Active Ulcerative Colitis, *Gastroenterology* (1994), 106:A705.
Larson et al., "1,25(OH)$_2$–D$_3$ is a Potent Regulator of Interleukin–1 Induced Interleukin–8 Expression and Production," *Biochem. BIophys. Res. Comm.* (1991), 176(3):1020–1026.
McDonald, T.T., "Epithelial Proliferation in Response to Gastrointestinal Inflammation," *Ann. NY Acad. Sci.,* (1992), 664:202–209.
Marchuk et al., "Construction of T–vectors, a rapid and general systems for direct cloning of unmodified PCR products", *Nuc. Acids Res.* (1991), 19:1154.
Murdoch et al., "Calcipotriol: A Review of its Pharmacological Properties and Therapeutic Use in Psoriasis Vulgaris," *Drugs* (1992), 43(3):415–429.
Nudelman et al., "Novel Anticancer Prodrugs of Butyric Acid", *J. Med. Chem.* (1992), 35(4):687–694.
Planchone et al., "Differential Elimination of Synthetic Butyric Triglycerides In Vivo: A Pharmcokinetic Study", *J. Pharm. Sci.* (1993), 82:1046–1048.
Pols et al., "Vitamin D Analogues: From Molecule to Clinical Application," *Clin. Endocrin.* (1994), 40:285–291.
Radema et al., "Interleukin 1β is Expressed Predominantly by Enterocytes in Experimental Colitis," *Gastroenterology* (1991), 100:1180–1186.
Risio, M., "Cell Proliferation in Colorectal Tumor Progression: An Immunohistochemical Approach to Intermediate Biomarkers", *J. Cell Biochem.* (1992), 16G:79–87.
Samid et al., "Selective Growth Arrest and Phenotypic Reversion of Prostate Cancer Cells in Vitro by Nontoxic Pharmacological Concentrations of Phenylacetate," *J. Clin. Invest.* (1993), 91:2288–2295.
Scheppach et al., "Effect of Butyrate Enemas on the Colonic Mucosa in Distal Ulcerative Colitis," *Gastroenterology* (1992), 103:51–56.
Serafini et al., "Rate and pattern of epithelial cell proliferation in ulcerative colits," *Gut* (1981), 22:648–652.
Snyderman et al., "The Absorption of Short–Chain Fats By Premature Infants", *Arch. Dis. Child.* (1955), 30:83–84.
Steinhart et al., "Treatment of Refractory Ulcerative Proctosigmoiditis with Butyrate Enemas",*Am. J. Gastro.* (1994), 89:179–183.

(List continued on next page.)

*Primary Examiner*—Gary L. Kunz
*Attorney, Agent, or Firm*—Law Offices of Jane Massey Licata

[57] ABSTRACT

A method for decreasing the inflammation associated with a chronic inflammatory intestinal condition in a patient is provided wherein the patient is administered an effective amount of a differentiating agent.

1 Claim, 1 Drawing Sheet

OTHER PUBLICATIONS

Thibault et al., "A Phase I and Pharmacokinetics Study of Intravenous Phenylacetate in Patients with Cancer," *Cancer Res.* (1994), 54:1690–1694.

Traber et al., "Novel DNA–Binding Proteins Regulate Intestine–Specific Transcription of the Scurase–Isomaltase Gene", *Mol. Cell. Biol.* 12:3614–3627, 1992.

Traber et al., "Sucrase–isomaltase gene expression along crypt–villus axis of human small intestine is regulated at level of mRNA abundance", *Am. J. Physiol.*, 262:G123–G130, 1992.

Wu et al., "Sucarse–Isomaltase Gene Expression in Barrett's Esophagus and Adenocarcinoma", *Gastroenterology* (1993), 105:837–844.

Wu et al., "Isolation and Characterization of the Human Scurase–Isomaltase Gene and Demonstrationl of Intestine–Specific Transcriptional Elements," *J. Biol. Chem.* 267:7863–7870, 1992.

DIFFERENTIATING AGENTS FOR THE TREATMENT OF INFLAMMATORY INTESTINAL DISEASES

This application is a continuation-in-part of application Ser. No. 08/387,116 filed Feb. 13, 1995, now U.S. Pat. No. 5,569,680.

BACKGROUND OF THE INVENTION

Neoplastic disease is characterized by inappropriate cell proliferation relative to the rate of differentiation. A variety of agents which can induce transformed cells to express characteristics of a differentiated state and cease proliferating have been identified for use in the treatment of human cancers. Such agents include relatively simple polar/apolar compounds, retinoic acid and its derivatives, vitamin $D_3$ and its derivatives, tumor promoters, inhibitors of RNA or DNA synthesis including several agents used as cytotoxic therapy for cancers, growth factors, such as hematopoietic-cell growth factors, proteases, and hormones. The basic defect in cancers involves an imbalance in the relationship between proliferation of precursor cells and the differentiation of these cells. Differentiation factors can normalize the relationship of proliferation to differentiation. Consideration of a use for differentiating factors in the treatment of human cancers is based largely upon in vitro studies that have demonstrated the effectiveness of these agents in inducing a wide variety of transformed cell lines to differentiate and stop growing. The successful treatment of human acute promyelocytic leukemia by retinoic acid established that cytodifferentiation therapy may have utility in the treatment of human malignancies. The clinical evaluation of additional differentiating agents has begun more recently.

Butyric acid has been shown to induce cytodifferentiation in vitro in a wide variety of neoplastic cells. Chen, Z. and Brutman, T. R. *Cancer Res.* 1994, 54:3494–3499. The potential utility of this agent as an antineoplastic has been limited, however, by the apparent difficulty in achieving effective concentrations of butyric acid in vivo. Chen and Brutman studied the effect of the prodrugs monobutyrin and tributyrin in vitro in inducing differentiation of human myeloid leukemia HL60 cells and murine erythroleukemia cells. Butyric acid, monobutyrin and tributyrin all induced erythroid differentiation of erythroleukemia. However, on a molar basis tributyrin was 3- to 4-fold more potent than butyric acid, whereas monobutyrin was much less potent than butyric acid. Based upon these experiments, it was suggested that tributyrin may be a promising candidate as a prodrug of butyric acid, either as a sole agent or in combination with other agents, for cytodifferentiation therapy of human leukemia and other malignancies and possibly for patients with β-hemoglobinopathies. Chen, Z. and Brutman, T. R. *Cancer Res.* 1994, 54:3494–3499.

Another differentiating agent, sodium phenylacetate, has been evaluated as an alternative to cytotoxic chemotherapy in the treatment of cancer. Phenylacetate has been demonstrated to promote maturation of various human leukemic cell lines. In addition, its use has been suggested in the treatment of prostate cancer. Samid et al. *J. Clin. Invest.* 1993, 91:2288–2295. Phenylacetate has been demonstrated to suppress tumor growth and promote differentiation in experimental models. Thibault et al. *Can. Res.* 1994, 54:1690–1694. It has also been shown that sodium phenylacetate and its precursor, sodium 4-phenylbutyrate, enhance fetal hemoglobin production in cultured erythroid progenitor derived from normal donors and patients with sickle cell anemia and β-thalassemia.

There is also increasing evidence to suggest that 1,25-dihydroxy vitamin $D_3$ (1,25-$(OH)_2D_3$), or calcitriol, has important physiological effects on growth and differentiation in a variety of malignant and nonmalignant cell types. One of the earliest demonstrations of the antiproliferative effects of 1,25-$(OH)_2D_3$ was with the HL-60 human promyelocytic leukemia cell line. Treatment with physiological doses of 1,25$(OH)_2D_3$ suppressed cell growth and induced monocytic differentiation. Similar growth-inhibiting and differentiation-inducing effects have been demonstrated in vitro in other cell types including normal human bone cells, and in malignant cell lines derived from breast, malignant melanoma, histiocytic lymphoma and colon carcinoma. Halline et al. *Endocrinology* 1994, 134(4):1710–1717.

Differentiating agents such as 1,25$(OH)_2D_3$ and analogs thereof, have also been used in the treatment of diseases related to disordered epidermal differentiation. In addition to producing vitamin D, epidermal cells (keratinocytes) make 1,25$(OH)_2D_3$, contain 1,25$(OH)_2D_3$, and respond to 1,25 $(OH)_2D_3$ with changes in proliferation and differentiation. Bikle, D. D. and Pillai, S. *Endocrine Reviews* 1993, 14(1):3–19. 1,25$(OH)_2D_3$ has been found to inhibit IL-1α induced IL-8 production and mRNA expression in keratinocytes, fibroblasts and PBMC, but not in endothelial cells. Larsen et al. *Biochem. Biophys. Res. Commun.* 1991, 176(3) 1020–1026. Calcipotriol is a vitamin $D_3$ analog which also inhibits cell proliferation and enhances cell differentiation. Calcipotriol has pharmacodynamic properties similar to those of calcitriol, the active metabolite of vitamin $D_3$. In several in vitro models both calcipotriol and calcitriol inhibit cell proliferation and enhance cell differentiation. Both drugs reduce cell numbers, total DNA content and incorporation of radiolabeled thymidine into DNA and increase the number of human keratinocytes with cornified envelopes and activity of enzyme-caused, protein crosslinking in the envelopes. In patients with psoriasis, calcipotriol also reduces dermal proliferation and enhances differentiation in lesional skin. Murdoch, D. and Clissold, S. P. *Drugs* 1992, 43(3):415–429.

It has now been found that differentiating agents are also useful in the treatment of intestinal inflammatory diseases. Differentiating agents which alter the state of proliferation and ultimately the differentiation of colonic epithelial cells reduce the inflammation associated with intestinal diseases such as ulcerative colitis.

SUMMARY OF THE INVENTION

An object of the present invention is to provide a method of treating intestinal inflammatory diseases in a patient by administering to a patient an effective amount of a differentiating agent.

DETAILED DESCRIPTION OF THE INVENTION

Figure 1:
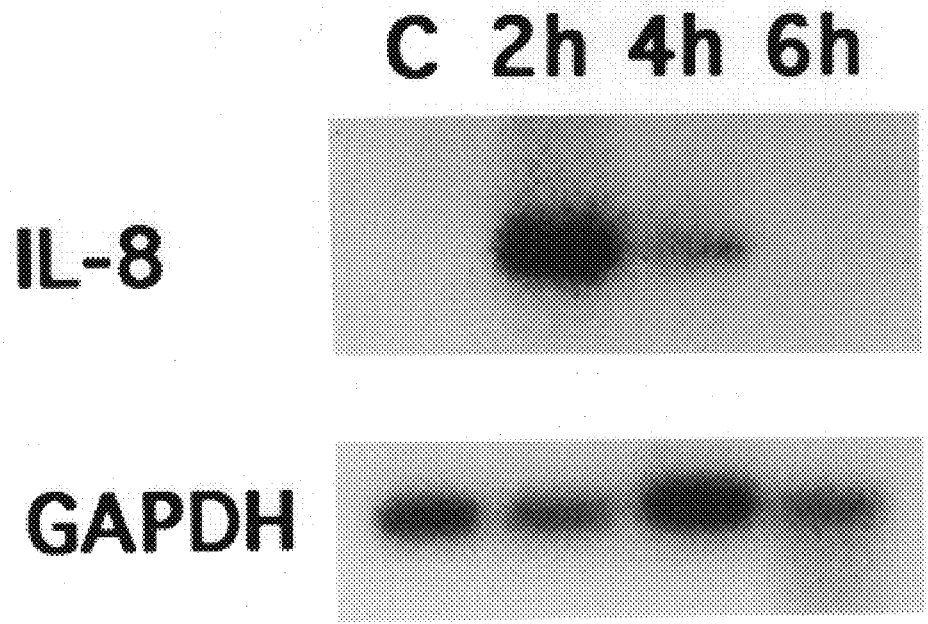
FIG. 1 is a Northern blot of total RNA from preconfluent undifferentiated Caco-2 cells stimulated with IL-1β which is hybridized with a cDNA probe for IL-8 and then rehybridized with a cDNA probe for 7S to demonstrate the loading and integrity of the RNA in each lane.

The normal mammalian small intestine is lined by an epithelium that is continuously renewed by proliferation of stem cells in intestinal crypts, migration of daughter cells from crypts onto villi, and extrusion of cells into the intestinal lumen at the tips of villi. Migration of enterocytes from crypts to villi is coincident with the appearance of a differentiated phenotype. Accordingly, the intestinal mucosa represents a dynamic, complex epithelium that is spatially segregated into a proliferating, undifferentiated compartment referred to as the crypts and a nonproliferating, differentiated compartment referred to as the villi. Gordon, J. I. *J. Cell. Biol.* 1989, 108:1187–1194. A similar compartmentalization occurs in the large intestine with undifferentiated proliferating epithelial cells located in the lower ⅔rds of the colonic crypts and undifferentiated cells located in the upper 3rd as well as on the surface mucosa. Risio, M. *J. Cell. Biochem.* 1992, 16G:79–87; Barnard et al. *Gastroenterology* 1993, 105:67–73.

During intestinal inflammatory states, however, there is an alteration in this pattern of epithelial differentiation. There is an increase in epithelial proliferation with an expansion of cell populations in an undifferentiated state, referred to as crypt hypertrophy, as well as a decrease in cells exhibiting a differentiated phenotype, referred to as villus atrophy. This histologic pattern has been observed in many small intestinal inflammatory states such as celiac disease, pouchitis, tropical sprue and giardiasis. MacDonald, T. T. *Ann. NY Acad. Sci.* 1992, 664:202–209. A hyperproliferative state also occurs in the colonic epithelium during inflammatory states such as ulcerative colitis and parasitic infections. Risio, M. *J. Cell. Biochem.* 1992, 16G:79–87.

It is believed that the expansion of the crypt cell compartment helps to perpetuate the intestinal inflammatory response. Indirect evidence suggests that the state of epithelial cell differentiation may determine whether or not intestinal epithelia are capable of responding to an inflammatory stimulus. Studies have shown that only undifferentiated proliferating crypt cells are capable of producing inflammatory cytokines such as IL-8 (Izzo et al. *Gastroenterology* 1994, 106:A239) and IL-1β (Radema et al. *Gastroenterology* 1991, 100:1180–1186). Furthermore, the production of neutrophil chemoattractive substances such as IL-8 exclusively by the crypt epithelium may explain why transmigration of neutrophils in acute intestinal inflammatory states occurs in the crypt compartment referred to as crypt abscesses. In addition, induction of MHC class 2 expression by the intestinal epithelium in response to interferon γ or other inflammatory states such as GVDH or *Trichinella spiralis* infection occurs only in the proliferating crypt epithelium in both the small and large intestine. Bland, P. *Immunology Today* 1988, 9:174–178.

The histologic appearance of active ulcerative colitis includes an intense lymphoplasmocytosis limited to the mucosa and submucosa which may be associated with a neutrophilic infiltrate invading the colonic epithelium, in particular the crypt abscess. This intense neutrophilic infiltrate observed with acute ulcerative colitis has been associated with elevated mucosal levels of interleukin-8 and circulating antibodies in patients with active ulcerative colitis as compared to normal controls and patients with active Crohn's disease. Hawkeyk et al. *Agents Actions* 1992, 92:C23–26. Ulcerative colitis is therefore categorized as a disorder of the colonic mucosa. Several investigators have shown that the colonic epithelium is in a hyperproliferative state with expansion of the proliferative compartment from the lower crypt to the upper crypt extending to the surface epithelium. Biasco et al. *Cancer Res.* 1984, 44:5450–5454; Serafini et al. *Gut* 1981, 22:648–652. This hyperproliferative state is independent of the degree of inflammation and the duration of the disease, and exists even when the disease is in an inactive state, thus suggesting an intrinsic abnormality of the colonic epithelium in ulcerative colitis. Biasco et al. *Cancer Res.* 1984, 44:5450–5454; Serafini et al. *Gut* 1981, 22:648–652. Similar hyperproliferative states have been observed in patients at risk for colonic malignancy such as in familial polyposis coli, sporadic adenomas and familial nonpolyposis colon cancer. Risio, M. *J. Cell. Biochem.* 1992, 16G:79–87.

It has now been found that the ability of intestinal epithelial cells to respond to an inflammatory stimulus such as that resulting from ulcerative colitis is dependent on the state of cell differentiation. It has been demonstrated that undifferentiated or pre-confluent Caco-2 cells can be stimulated by interleukin-1β (IL-1β) to produce interleukin-8 (IL-8) mRNA. In contrast, differentiated or post-confluent cells produce very little IL-8 mRNA after stimulation. It has also been found that nutrients and their derivatives, such as butyrate and vitamin D, which are capable of inducing differentiation, inhibit the expression of inflammatory mediators by intestinal epithelial cells. Induction of Caco-2 cell differentiation using differentiating agents such as sodium butyrate or vitamin D inhibits the expression of IL-8.

Butyrate enemas have been used to reduce inflammation in patients with distal ulcerative colitis. Breuer et al. *Dig. Dis. Sci.* 1991, 36:185–187; Scheppach et al. *Gastroenterology* 1992, 103:51–56; Steinhart et al. *Am. J. Gastro.* 1994, 89:179–183. In two studies, butyrate enemas were shown to result in a significant clinical response in patients whose disease did not respond to traditional forms of treatment including use of corticosteroids and 5-amino salicylic acid compounds. The basis of this response is unknown. Scheppach et al. observed that the labeling index of clonocytes in the upper crypt of patients with ulcerative colitis fell to that of normal healthy controls after treatment with butyrate enemas. However, the use of butyrate enemas is severely limited due to its extremely strong odor which leads to patients refusing to continue treatment.

The metabolically active form of vitamin D, 1,25-dihydroxyvitamin $D_3$ [1,25-$(OH)_2D_3$] or calcitrol, has also been recognized as a differentiation agent. This form of vitamin D not only plays a critical role in calcium and phosphorus homeostasis, but also inhibits cell proliferation and induces differentiation of multiple malignant as well as non-transformed cell types. Pols et al. *Clinical Endocrinology* 1994, 40:285–291.

In vitro data have now demonstrated that differentiating agents such as sodium butyrate, sodium propionate, 1,25-$(OH)_2D_3$, and phenylacetate are capable of inducing intestinal epithelial cell differentiation concurrent with inhibiting gene expression for the proinflammatory cytokine IL-8. Tributyrin, a less noxious prodrug of sodium butyrate, has also been shown to lead to an identical biological response in vitro at concentrations one third (⅓) that of sodium butyrate. These results were unexpected in light of in vitro experiments related to cytodifferentiation wherein it was found that tributyrin was only as effective as sodium butyrate in inhibiting cell proliferation at the same dose. Nudelman et al. *J. Med. Chem.* 1992, 35(4):687–694. Furthermore, these results suggest that colonic epithelial cells contain intracellular esterases that allow tributyrin to be metabolized to butyrate. No toxicity has been observed in mice treated with tributyrin either orally or intraperitoneally with a dose of 26.5 mmole/kg. Planlchon et al. *J. Pharm. Sci.* 1993, 82:1046–1048. In addition, tributyrin has been well tolerated in humans. For example, no detectable side effects were seen after six premature infants were fed butyrates for 4 days at doses of about 20 mmol/kg/day. Snyderman et al. *Arch Dis. Child.* 1955, 30:83–84.

In the present invention, a method is provided for decreasing the inflammation associated with a chronic inflammatory intestinal condition in a patient which comprises administering to a patient an effective amount of a differentiating agent. Examples of differentiating agents which can influence the inflammatory states of the intestine include, but are not limited to, polar/apolar compounds such as dimethyl sulfoxide and hexamethylene bisacetamide; retinoids such as 13-cis-retinoic acid, all-trans-retinoic acid and other analogs of retinol; vitamin D analogs including 1,25-$(OH)_2D_3$; histone hyperacetylators such as sodium butyrate and pro-drugs thereof, sodium propionate and trichostatin A; hormones such as TGF-β and glucocorticoids; antioxidants such as PDTC; peroxisome proliferators such as clofibrate; and miscellaneous differentiating agents such as phenylacetate and phenylbutyrate. By "effective amount" it is meant a concentration sufficient to decrease the inflammation in the intestine associated with the condition. Effective concentrations of a differentiating agents can be easily determined based upon the data provided in the instant disclosure and knowledge of those of skill in the art. By "patient" it is meant an individual suffering from a chronic intestinal inflammatory condition. Examples of diseases or conditions which can be treated with the differentiating agents in accordance with the present invention include, but are not limited to, ulcerative colitis, Crohn's disease, Type A chronic gastritis, Type B chronic gastritis and graft vs. host disease (GVDH).

Once the inflammatory state has been initiated, an entire cascade of inflammatory mediators including cytokines, complement factors, prostaglandins, bradykinins and oxygen radicals follows. Accordingly, attempts to inhibit a single inflammatory pathway will not always lead to resolution of inflammation once the reaction has been initiated. An example of this is the inability of IL-1 receptor antagonists to induce clinical remission in patients with active ulcerative colitis. In contrast, antiinflammatory agents such as glucocorticoids which inhibit multiple inflammatory pathways simultaneously, have been shown to be very effective in the treatment of inflammatory disease of the bowel. Thus, it is believed that the administration of differentiating agents which inhibit the expression of inflammatory mediators by epithelial cells in conjunction with inhibitors of inflammatory mediators produced by immunocytes such as IL-1 receptor antagonist and cyclosporin, will result in a synergistic anti-inflammatory effect.

The following nonlimiting examples are provided to further illustrate the present invention.

EXAMPLES

Example 1

Induction of IL-8 mRNA in Caco-2 Cells

Caco-2 cells (American Type Culture Collection, Rockville, Md.) were plated at a density of $4 \times 10^4$ cells per $cm^2$ in 10 cm dishes containing Dulbecco's modified Eagle's medium (DMEM) with 10% fetal bovine serum and penicillin/streptomycin as described by Wu et al. *J. Biol. Chem.* 1992, 267:7863–7870 and Traber et al. *Mol. Cell. Biol.* 1992, 12:3614–3627. At days 5 (pre-confluent state) and 18 (post-confluent state) the cells were stimulated with complete medium containing 5 ng/ml of IL-1β (R and D Systems, Minneapolis, Minn.). Total RNA was isolated from these cells 2 and 4 hours after the addition of IL-1β containing medium as well as from a control cell population not treated with IL-1β in accordance with procedures described by Chomczynski, P. and Sacchi, *N. Anal. Biochem.* 1987, 162:156–159. Ten micrograms of RNA for each sample was electrophoretically separated, transferred to a nylon membrane, and UV crosslinked in accordance with procedures described by Traber et al. *Am. J. Physiol.* 1992, 262:G123–G130. A cDNA probe for IL-8 was prepared by RT-PCR of total RNA from Caco-2 cells stimulated with IL-1β for 2 hours. Random hexamers were used for reverse transcription of the RNA using reaction conditions similar to those described by Wu et al. *Gastroenterology* 1993, 105:837–844. A 277 bp cDNA was amplified from the RT reaction by PCR using the 5' primer IL-8(+103) and the 3' primer IL-8(EX4), cloned using a TA-vector (Marchuk et al. *Nuc. Acids Res.* 1991, 19:1154), and labeled with $^{32}P$ using a Random Primers DNA labeling System (Gibco BRL, Gaithersburg, Md.). Hybridization of the Northern blots were performed using conditions as described by Huang et al. *Mol. Endo.* 1993, 7:1391–1398.

IL-8(+103)
5'-GTGGGATCCATGACTTCCAAGCTGGCC-3'(SEQ ID NO: 1)
IL-8(EX4) 5'-GTGGGATCCGAATTCTCAGCCCTCTTC-3'(SEQ ID NO: 2)
GGATCC indicates the BAM HI site.
Results are shown in FIG. 1.

Figure 2:
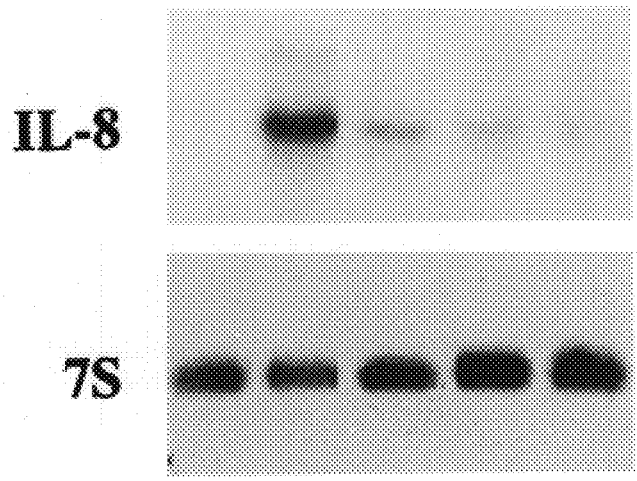
FIG. 2 is a Northern blot of the same RNA samples as shown in FIG. 1 which is hybridized using a probe for a fragment of the CCAAT/Enhancer Binding Protein delta isoform, an immediate gene product of the inflammatory response, and then rehybridized with a probe for 7S ribosomal RNA to demonstrate the loading and integrity of the RNA in each lane.

FIG. 2 shows a second Northern blot using the same total RNA hybridized with a 1.3 kb (Eco R1/Mlu1) restriction fragment of the CCAAT/Enhancer Binding Protein delta (C/EBPδ) isoform. Cao et al. *Genes and Develop.* 1991, 5:1538–1552. Both blots were subsequently stripped and rehybridized with a cDNA probe for 7S ribosomal RNA to demonstrate the loading and integrity of the RNA in each lane.

Stimulation of pre-confluent undifferentiated Caco-2 cells with IL-1β lead to a dramatic induction of IL-8 mRNA at 2 hours which rapidly decreased at late time points (see FIG. 1). In contrast, stimulation of post-confluent differentiated Caco-2 cells showed very minimal induction of IL-8 mRNA (see FIG. 1). Hybridization of this same RNA using a probe for C/EBPδ, an immediate gene product of the inflammatory response, demonstrated that post-confluent Caco-2 cells actually produce greater amounts of this mRNA than pre-confluent cells. Thus, although post-confluent Caco-2 cells are still capable of responding to an inflammatory status, it appears that the expression of a gene encoding an inflammatory modulating substance such as IL-8 is differentially regulated. Furthermore, the C/EBPδ response of post-confluent cells suggests that functional IL-1β is present in the medium of post-confluent Caco-2 cells and that functional IL-1β receptors as well as a signal transduction pathway must still exist in post-confluent Caco-2 cells.

Example 2

Inhibition of IL-1β Stimulated IL-8 Gene Expression With Differentiating Agents Approximately 18 hours post-plating, Caco-2 cells were placed in complete medium containing various concentrations of sodium butyrate (Sigma Chemical Company, St. Louis, Mo.), sodium propionate (Sigma Chemical Company, St. Louis, Mo.), 1,25-$(OH)_2D_3$ (Biomol Research Laboratories, Plymouth Meeting, Pa.) or phenylacetate (Sigma Chemical Company, St. Louis, Mo.). Caco-2 cells were also plated that were not treated with any of these compounds. The medium was changed on a daily basis for 3 days. On day 5 all the cells (except for control) were stimulated with IL-1β (5 ng/ml) for 2 hours. Total RNA was then isolated and Northern blots performed as described in Example 1. The blots were hybridized to the IL-8 cDNA probe also described in Example 1.

Increasing concentrations of sodium butyrate from 0.1 to 2.5 mM led to a dose dependent reduction in steady state levels of IL-8 mRNA. These concentrations of sodium butyrate were well-tolerated by Caco-2 cells without any evidence of cell death. Treatment of Caco-2 cells with sodium butyrate at concentrations higher than 2.5 mM, which caused significant toxicity and cell death, led to increased expression of IL-8 mRNA. Concurrent with maximal inhibition of IL-8 mRNA expression at 2.5 mM is the induction of mRNA for alkaline phosphatase, a marker for intestinal epithelial cell differentiation.

Sodium propionate (0.1 to 20 mM) also inhibited IL-8 mRNA expression in a dose dependent fashion concurrent with the induction of alkaline phosphatase mRNA expression. In contrast to sodium butyrate, however, treatment of Caco-2 cells with the maximum concentration of sodium propionate studied, 20 mM, did not lead to cell toxicity or death.

1,25-$(OH)_2D_3$ at concentrations of $10^{-8}$ and $10^{-9}$ also caused a decrease in steady state IL-8 mRNA expression. These concentrations of 1,25-$(OH)_2D_3$ have also been shown to inhibit Caco-2 cell proliferation and induce markers of intestinal epithelial differentiation. Halline et al. *Endocrinology* 1994, 134:1710–1717.

Dose dependent inhibition of IL-8 mRNA expression was also observed with phenylacetate at concentrations ranging from 2.5 to 10 mM. There was no evidence of Caco-2 cell toxicity at any concentration of phenylacetate studied.

---

---

What is claimed is:

1. A method for decreasing the elevated levels of interleukin-8 in chronic inflammatory intestinal conditions comprising administering an effective amount of a differentiating agent selected from the group consisting of sodium proprionate and hexamethylene bisacetamide.

\* \* \* \* \*

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 27
      (B) TYPE: Nucleic Acid
      (C) STRANDEDNESS: Single
      (D) TOPOLOGY: Linear (iv) ANTI-SENSE: No (xi) SEQUENCE DESCRIPTION: SEQ ID NO: 1:

GTGGGATCCA TGACTTCCAA GCTGGCC                        27

(2) INFORMATION FOR SEQ ID NO: 2:

(i) SEQUENCE CHARACTERISTICS:
      (A) LENGTH: 27
      (B) TYPE: Nucleic Acid
      (C) STRANDEDNESS: Single
      (D) TOPOLOGY: Linear (iv) ANTI-SENSE: No (xi) SEQUENCE DESCRIPTION: SEQ ID NO: 2:

GTGGGATCCG AATTCTCAGC CCTCTTC                        27